United States Patent [19]

Ayres et al.

[11] 4,427,675
[45] Jan. 24, 1984

[54] CEPHALOSPORIN ANTIBIOTICS

[75] Inventors: Barry E. Ayres, Ickenham; Cynthia H. O'Callaghan, Gerrards Cross; David G. H. Livermore, Princes Risborough; Christopher E. Newall, London, all of England

[73] Assignee: Glaxo Group Limited, London, England

[21] Appl. No.: 306,729

[22] Filed: Sep. 29, 1981

Related U.S. Application Data

[63] Continuation of Ser. No. 193,844, Oct. 3, 1980, abandoned, which is a continuation of Ser. No. 123,566, Feb. 22, 1980, abandoned.

[30] Foreign Application Priority Data

Feb. 23, 1979 [GB] United Kingdom ................ 7906478
Feb. 23, 1979 [GB] United Kingdom ................ 7906479

[51] Int. Cl.³ ................ C07D 501/38; A61K 31/545
[52] U.S. Cl. ................................ 424/246; 544/22; 544/26; 544/27
[58] Field of Search ........................ 544/26, 27, 22; 424/246

[56] References Cited

U.S. PATENT DOCUMENTS 4,165,430 8/1979 Bradshaw et al. .................... 544/27
4,298,606 11/1981 Ochiai et al. ......................... 544/27

Primary Examiner—Nicholas S. Rizzo
Attorney, Agent, or Firm—Bacon & Thomas

[57] ABSTRACT

Cephalosporin antibiotics of general formula

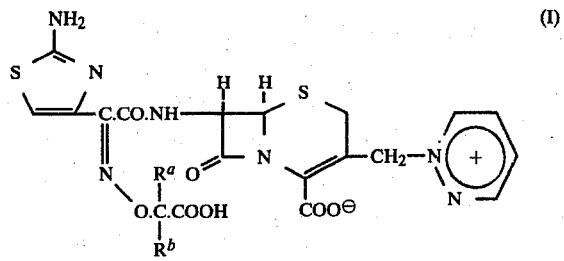

(I)

(wherein $R^a$ and $R^b$, which may be the same or different, each represent a $C_{1-4}$ alkyl group, or together with the carbon atom to which they are attached form a $C_{3-7}$ cycloalkylidene group). These compounds exhibit broad spectrum antibiotic activity, the activity being unusually high against gram-negative organisms such as strains of Pseudomonas organisms.

Particularly effective compounds of formula (I) are (6R,7R)-7-[(Z)-2-(2-aminothiazol-4-yl)-2-(2-carboxyprop-2-oxyimino)acetamio]-3-(pyridazinium-1-ylmethyl)ceph-3-em-4-carboxylate and (6R,7R)-7-[(Z)-2-(2-aminothiazol-4-yl)-2-(t-carboxycyclobut-1-oxyimino)acetamido]-3-(pyridazinium-1-ylmethyl)-ceph-3-em-4-carboxylate. The invention also includes the non-toxic salts and non-toxic metabolically labile esters of compounds of formula (I), compositions containing the antibiotic compounds of the invention and a method of combatting bacterial infection utilizing the antibiotics.

9 Claims, No Drawings

CEPHALOSPORIN ANTIBIOTICS

This application is a continuation of application Ser. No. 193,844, filed Oct. 3, 1980, now abandoned which is a continuation of Ser. No. 123,566, filed Feb. 22, 1980, now abandoned.

The present invention provides cephalosporin antibiotics of the formula:

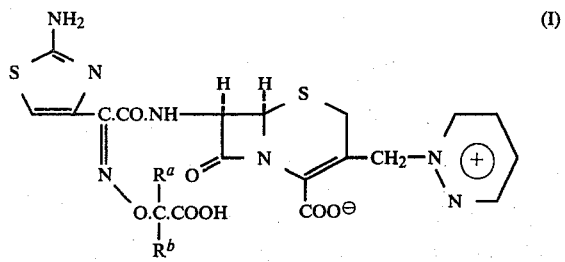

(wherein $R^a$ and $R^b$, which may be the same or different, each represents a $C_{1-4}$ alkyl group, preferably a straight chain alkyl group, i.e. a methyl, ethyl, n-propyl or n-butyl group and particularly a methyl or ethyl group, or, together with the carbon atom to which they are attached, form a $C_{3-7}$ cycloalkylidene group preferably a $C_{3-5}$ cycloalkylidene group and non-toxic salts and non-toxic metabolically labile esters thereof.

The cephalosporin compounds in this specification are named with reference to "cepham" after *J. Amer. Chem. Soc.*, 1962, 84, 3400, the term "cephem" referring to the basic cepham structure with one double bond.

The compounds according to the invention are syn isomers. The syn isomeric form is defined by the configuration of the group

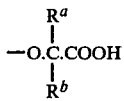

with respect to the carboxamido group. In this specification the syn configuration is denoted structurally as

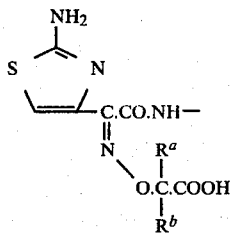

It will be understood that since the compounds according to the invention are capable of geometric isomerism, some admixture with the corresponding anti isomer may occur.

The invention also includes within its scope the solvates (especially the hydrates) of the compounds of formula (I). It also includes within its scope salts of esters of compounds of formula (I).

The compounds according to the present invention may exist in tautomeric forms (for example in respect of the 2-aminothiazolyl group) and it will be understood that such tautomeric forms, e.g. the 2-iminothiazolinyl form, are included within the scope of the invention.

Moreover, the compounds of formula (I) depicted above may also exist in alternative zwitterionic forms, for example wherein the 4-carboxyl group is protonated and the terminal carboxyl group in the 7-side chain is deprotonated. Such zwitterionic forms and mixtures thereof are included within the scope of the present invention.

It will also be appreciated that when $R^a$ and $R^b$ in formula (I) represent different $C_{1-4}$ alkyl groups the carbon atom to which they are attached will comprise a centre of asymmetry. Such compounds are diastereoisomeric and the present invention embraces individual diasteroisomers of these compounds as well as mixtures thereof.

The compounds according to the invention exhibit broad spectrum antibiotic activity against a wide range of commonly encountered pathogenic organisms. Against gram-negative organisms the activity is unusually high. This high activity extends to many $\beta$-lactamase-producing gram-negative strains. The compounds also possess high stability to $\beta$-lactamases produced by a range of gram-positive and gram-negative organisms.

Compounds according to the invention have been found to exhibit unusually high activity against strains of Pseudomonas organisms, e.g. strains of *Pseudomonas aeruginosa* as well as high activity against various members of the Enterobacteriaceae (e.g. strains of *Escherichia coli, Klebsiella pneumoniae, Salmonella typhimurium, Enterobacter cloacae, Serratia marcescens,* Providence species, *Proteus mirabilis* and especially indole positive Proteus organisms such as *Proteus vulgaris* and *Proteus morganii*), and strains of *Haemophilus influenzae*.

The antibiotic properties of the compounds according to the invention compare very favourably with those of the aminoglycosides such as amikacin or gentamicin. In particular, this applies to their activity against strains of various Pseudomonas organisms which are not susceptible to many existing commercially available antibiotic compounds. Unlike the aminoglycosides, cephalosporin antibiotics normally exhibit low toxicity in man. The use of aminoglycosides in human therapy tends to be limited or complicated by the relatively high toxicity of these antibiotics. The cephalosporin antibiotics of the present invention thus possess potentially great advantages over the aminoglycosides.

Non-toxic salt derivatives which may be formed from the compounds of general formula (I) include inorganic base salts such as alkali metal salts (e.g. sodium and potassium salts) and alkaline earth metal salts (e.g. calcium salts); amino acid salts (e.g. lysine and arginine salts); organic base salts (e.g. procaine, phenethylbenzylamine, dibenzylethylenediamine, ethanolamine, diethanolamine and N-methyl-glucosamine salts). Other non-toxic salt derivatives include acid addition salts, e.g. formed with hydrochloric, hydrobromic, sulphuric, nitric, phosphoric, formic and trifluoroacetic acids. The salts may also be in the form of resinates formed with, for example, a polystyrene resin or cross-linked polystyrene divinylbenzene copolymer resin containing amino or quaternary amino groups or sulphonic acid groups, or with a resin containing carboxyl groups, e.g. a polyacrylic acid resin. Soluble base salts (e.g. alkali metal salts such as the sodium salt) of compounds of formula (I) may be used in therapeutic applications because of the rapid distribution of such salts in the body upon administration. Where, however, insoluble salts of compounds (I) are desired in a particular application, e.g. for use in depot preparations, such salts may be formed in conventional manner, for example with appropriate organic amines.

These and other salt derivatives such as the salts with toluene-p-sulphonic and methanesulphonic acids may be employed as intermediates in the preparation and/or purification of the present compounds of formula (I), for example in the processes described below.

Non-toxic metabolically labile ester derivatives which may be formed from the parent compound of formula (I) include acyloxyalkyl esters, e.g. lower alkanoyloxymethyl or -ethyl esters such as acetoxymethyl or -ethyl or pivaloyloxymethyl esters. In addition to the above ester derivatives, the present invention includes within its scope compounds of formula (I) in the form of other physiologically acceptable equivalents, i.e. physiologically acceptable compounds which, like the metabolically labile esters, are converted in vivo into the parent antibiotic compound of formula (I).

Preferred compounds according to the invention include those compounds of formula (I) wherein $R^a$ and $R^b$ both represent methyl groups or together with the carbon atom to which they are attached form a cyclobutylidene group i.e. (6R,7R)-7-[(z)-2-(2-aminothiazol-4-yl)-2-(2-carboxyprop-2-oxyimino)acetamido]-3-(pyridazinium-1-ylmethyl)ceph-3-em-4-carboxylate and (6R,7R)-7-[(z)-2-(2-aminothiazol-4-yl)-2-(1-carboxycyclobut-1-oxyimino)-acetamido]-3-(pyridazinium-1-ylmethyl) ceph-3-em-4-carboxylate, and their non-toxic salts and non-toxic metabolically labile esters.

Other compounds according to the present invention include those for example wherein both of the groups $R^a$ and $R^b$ are ethyl groups, or wherein one of $R^a$ and $R^b$ is methyl and the other is ethyl. Further examples are provided by those compounds in which $R^a$ and $R^b$ together with the carbon atom to which they are attached form a cyclopropylidene or a cyclopentylidine group.

The above described compounds of formula (I) may be used for treating a variety of diseases caused by pathogenic bacteria in human beings and animals, such as respiratory tract infections and urinary tract infections.

According to a further embodiment of the present invention we provide a process for the preparation of compounds of formula (I) as hereinbefore defined or non-toxic salts or non-toxic metabolically labile esters thereof which comprises (A) acylating a compound of the formula

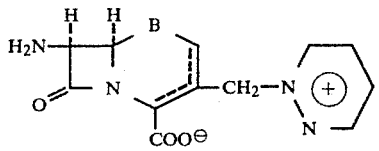

[wherein B is >S or >S→0 (α- or β-) and the dotted line bridging the 2-, 3- and 4-positions indicates that the compound is a ceph-2-em or ceph-3-em compound], or an acid addition salt (formed with, for example, a mineral acid such as hydrochloric, hydrobromic, sulphuric, nitric or phosphoric acid or an organic acid such as methane-sulphonic or toluene-p-sulphonic acid) or an N-silyl derivative thereof, or a corresponding compound possessing a group of the formula —COOR¹ at the 4-position where R¹ is a hydrogen atom or a carboxyl blocking group e.g. the residue of an ester-forming aliphatic or araliphatic alcohol or an ester-forming phenol, silanol or stannanol (the said alcohol, phenol, silanol or stannanol preferably containing 1 to 20 carbon atoms) and having an associated anion $A^-$ such as halide, e.g. chloride or bromide, or trifluoroacetate ion, with an acid of formula

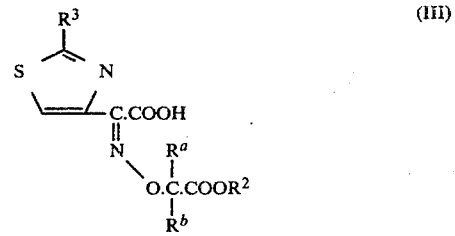

[wherein $R^a$ and $R^b$ are as hereinbefore defined; $R^2$ represents a carboxyl blocking group (e.g. as described for $R^1$) and $R^3$ is an amino or protected amino group] or with an acylating agent corresponding thereto, or (B) reacting a compound of formula

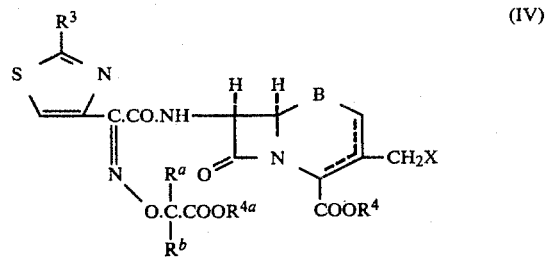

(wherein $R^a$, $R^b$, $R^3$, B and the dotted line are as hereinbefore defined; $R^4$ and $R^{4a}$ may independently represent hydrogen or a carboxyl blocking group; and X is a replaceable residue of a nucleophile, e.g. an acetoxy or dichloroacetoxy group or a halogen atom such as chlorine, bromine or iodine) or a salt thereof, with pyridazine; whereafter, if necessary and/or desired in each instance, any of the following reactions, in any appropriate sequence, are carried out:

(i) conversion of a $\Delta^2$-isomer into the desired $\Delta^3$-isomer, (ii) reduction of a compound wherein B is >S→0 to form a compound wherein B is >S, (iii) conversion of a carboxyl group into a non-toxic salt or non-toxic metabolically labile ester function, and (iv) removal of any carboxyl blocking and/or N-protecting groups.

In the above-described process (A), the starting material of formula (II) is preferably a ceph-3-em compound.

Acylating agents which may be employed in the preparation of compounds of formula (I) include acid halides, particularly acid chlorides or bromides. Such acylating agents may be prepared by reacting an acid (III) or a salt thereof with a halogenating agent e.g. phosphorus pentachloride, thionyl chloride or oxalyl chloride.

Where an acid addition salt of the compound of formula (II) is used, this is generally treated with a base prior to reaction with the compound of formula (III) or an acylating agent corresponding thereto.

Acylations employing acid halides may be effected in aqueous and non-aqueous reaction media conveniently at temperatures of from $-50°$ to $+50°$ C. preferably $-20°$ to $+30°$ C., if desired in the presence of an acid binding agent. Suitable reaction media include aqueous ketones such as aqueous acetone, esters such as ethyl acetate, halogenated hydrocarbons such as methylene chloride, amides such as dimethylacetamide, nitriles such as acetonitrile, or mixtures of two or more such solvents. Suitable acid binding agents include tertiary amines (e.g. triethylamine or dimethylaniline), inorganic bases (e.g. calcium carbonate or sodium bicarbonate), and oxidanes such as lower 1,2-alkylene oxides (e.g. ethylene oxide or propylene oxide) which bind hydrogen halide liberated in the acylation reaction.

Acids of formula (III) may themselves be used as acylating agents in the preparation of compounds of formula (I). Acylations employing acids (III) are desirably conducted in the presence of a condensing agent, for example a carbodiimide such as N,N'-dicyclohexylcarbodiimide or N-ethyl-N'-γ-dimethylaminopropylcarbodiimide; a carbonyl compound such as carbonyldiimidazole; or an isoxazolium salt such as N-ethyl-5-phenylisoxazolium perchlorate.

Acylation may be effected with other amide-forming derivatives of acids of formula (III) such as, for example, an activated ester, a symmetrical anhydride or a mixed anhydride (e.g. formed with pivalic acid or with a haloformate such as a lower alkylhaloformate).

Mixed anhydrides may also be formed with phosphorus acids (for example, phosphoric or phosphorous acids), sulphuric acid or aliphatic or aromatic sulphonic acids (for example toluene-p-sulphonic acid).

An activated ester may conveniently be formed in situ using, for example, 1-hydroxybenzotriazole in the presence of a condensing agent as set out above. Alternatively, the activated ester may be preformed.

Acylation reactions involving the free acids or their above mentioned amide-forming derivatives are desirably effected in an anhydrous reaction medium e.g. methylene chloride, tetrahydrofuran, dimethylformamide or acetonitrile.

If desired, the above acylation reactions may be performed in the presence of a catalyst, e.g. 4-dimethylaminopyridine.

The amino acids of formula (III) and acylating agents corresponding thereto may, if desired, be prepared and employed in the form of their acid addition salts. Thus, for example, acid chlorides may conveniently be employed as their hydrochloride salts and acid bromides as their hydrobromide salts.

In process (B) above, pyridazine may displace a wide variety of substituents X from the cephalosporin of formula (IV). To some extent the facility of the displacement is related to the pKa of the acid HX from which the substituent is derived. Thus, atoms or groups X derived from strong acids tend, in general, to be more easily displaced than atoms or groups derived from weaker acids.

The displacement of X by pyridazine may conveniently be effected by maintaining the reactants in solution or suspension. The reaction is advantageously effected using from 1 to 10 moles e.g. 1 to 5 moles of pyridazine in a suitable reaction medium. Alternatively pyridazine itself may be used as a solvent.

Nucleophilic displacement reactions may conveniently be carried out on those compounds of formula (IV) wherein the substituent X is a halogen atom or an acyloxy group, for example as discussed below.

Acyloxy groups

Compounds of formula (IV) wherein X is an acetoxy group are convenient starting materials for use in the nucleophilic displacement reaction with pyridazine. Alternative starting materials in this class include compounds of formula (IV) in which X is the residue of a substituted acetic acid e.g. chloroacetic acid, dichloroacetic acid and trifluoroacetic acid.

Displacement reactions on compounds of formula (IV) possessing X substituents of this class, particularly in the case where X is an acetoxy group, may be facilitated by the presence in the reaction medium of iodide or thiocyanate ions.

The substituent X may also be derived from formic acid, a haloformic acid such as chloroformic acid, or a carbamic acid.

When using a compound of formula (IV) in which X represents an acetoxy or substituted acetoxy group, it is generally desirable that the group $R^4$ in formula (IV) should be a hydrogen atom and that B should represent $>S$. In this case, the reaction is advantageously effected in an aqueous medium.

Under aqueous conditions, the pH value of the reaction solution is advantageously maintained in the range 6–8, if necessary by the addition of a base. The base is conveniently an alkali metal or alkaline earth metal hydroxide or bicarbonate such as sodium hydroxide or sodium bicarbonate.

When using compounds of formula (IV) in which X is an acetoxy group, the reaction is conveniently effected at a temperature of 0° C. to to 120° C., preferably 70° C. to 90° C.

The above described process employing compounds of formula (IV) in which X is the residue of a substituted acetic acid may be carried out as described in British patent specification No. 1,241,657.

Halogens

Compounds of formula (IV) in which X is chlorine, bromine or iodine atom can also be conveniently used as starting materials in the nucleophilic displacement reaction with pyridazine. When using compounds of formula (IV) in this class, B may represent $>S\rightarrow O$ and $R^4$ may represent a carboxyl blocking group. The reaction is conveniently effected in a non-aqueous medium which preferably comprises one or more organic solvents, advantageously of a polar nature such as ethers, e.g. dioxan or tetrahydrofuran, esters, e.g. ethyl acetate, amides, e.g. formamide or N,N-dimethylformamide or ketones e.g. acetone. Other suitable organic solvents are described in more detail in British patent specification No. 1,326,531.

In the case of reactions carried out on compounds of formula (IV) in which $R^4$ and $R^{4a}$ are carboxyl blocking groups the products will be formed as the corresponding halide salts which may, if desired, be subjected to one or more ion exchange reactions to obtain salts having the desired anion.

When using compounds of formula (IV) in which X is a halogen atom as described above, the reaction is conveniently effected at a temperature of 0° to +60°, preferably +15° to +30° C.

The reaction of the compound of formula (IV) with pyridazine may be carried out in the presence of an acid scavenging agent.

Pyridazine may, if desired, be added as an acid addition salt, e.g. the hydrochloride, where a base is present in the reaction medium to liberate free pyridazine. The base should of course be less nucleophilic than pyridazine to avoid competitive reaction with the compound of formula (IV).

The reaction product may be separated from the reaction mixture, which may contain, for example, unreacted nucleophile and other substances, by a variety of processes including recrystallisation, ionophoresis, column chromatography and use of ion-exchangers (for example by chromatography on ion-exchange resins) or macroreticular resins.

A Δ²-cephalosporin ester derivative obtained in accordance with the process of the invention may be converted into the corresponding Δ³-derivative by, for example, treatment of the Δ²-ester with a base such as pyridine or triethylamine.

A ceph-2-em reaction product may also be oxidised to yield the corresponding ceph-3-em 1-oxide, for example by reaction with a peracid e.g. peracetic or m-chloroperbenzoic acid; the resulting sulphoxide may, if desired, subsequently be reduced as described hereinafter to yield the corresponding ceph-3-em sulphide.

Where a compound is obtained in which B is >S→O this may be converted into the corresponding sulphide by, for example, reduction of the corresponding acyloxysulphonium salt prepared in situ by reaction with e.g. acetyl chloride in the case of an acetoxy-sulphonium salt, reduction being effected by, for example, sodium dithionite or by iodide ion as in a solution of potassium iodide in a water miscible solvent e.g. acetic acid, acetone, tetrahydrofuran, dioxan, dimethylformamide or dimethylacetamide. The reaction may be effected at a temperature between $-20°$ to $+50°$ C.

Metabolically labile ester derivatives of the compounds of formula (I) may be prepared by reacting a compound of formula (I) or a salt or protected derivative thereof with the appropriate esterifying agent such as an acyloxymethyl halide (e.g. iodide), conveniently in an inert organic solvent such as dimethylformamide or acetone, followed, where necessary, by removal of any protecting groups.

Base salts of the compounds of formula (I) may be formed by reacting an acid of formula (I) with an appropriate base. Thus, for example, sodium or potassium salts may be prepared using the respective 2-ethylhexanoate or hydrogen carbonate salts. Acid addition salts may be prepared by reacting a compound of formula (I) or a metabolically labile ester derivative thereof with the approprite acid.

Where a compound of formula (I) is obtained as a mixture of isomers, the syn isomer may be obtained by, for example, conventional methods such as crystallisation or chromatography.

For use as starting materials for the preparation of the compounds of formula (I) according to the invention, compounds of general formula (III) and acid halides and anhydrides corresponding thereto in their syn isomeric form, or in the form of mixtures of the syn isomers and the corresponding anti isomers containing at least 90% of the syn isomer, are preferably used.

Acids of formula (III) (provided that $R^a$ and $R^b$ together with the carbon atom to which they are attached do not form a cyclopropylidene group) may be prepared by etherification of a compound of formula

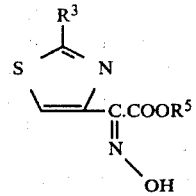

(wherein $R^3$ is as hereinbefore defined and $R^5$ represents a carboxyl blocking group) by reaction with a compound of general formula

(wherein $R^a$, $R^b$, and $R^2$ are as hereinbefore defined and T is halogen such as chloro, bromo, or iodo; sulphate; or sulphonate such as tosylate) followed by removal of the carboxyl blocking group $R^5$.

Acids of general formula (III) may also be prepared by reaction of a compound of formula

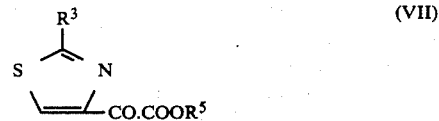

(wherein $R^3$ and $R^5$ are as hereinbefore defined) with a compound of formula

(wherein $R^a$, $R^b$ and $R^2$ are as defined above), followed by removal of the carboxyl blocking group $R^5$.

The last mentioned reaction is particularly applicable to the preparation of acids of formula (III) wherein $R^a$ and $R^b$ together with the carbon atom to which they are attached form a cylopropylidene group.

These methods of preparing the acids are described in more detail in Belgian patent specification No. 876538.

The acids of formula (III) may be converted to the corresponding acid halides and anhydrides and acid addition salts by conventional methods.

Where X is a halogen (i.e. chlorine, bromine or iodine) atom in formula (IV), ceph-3-em starting compounds may be prepared in conventional manner, e.g. by halogenation of a 7β-protected amino-3-methylceph-3-em-4-carboxylic acid ester 1β-oxide, removal of the 7β-protecting group, acylation of the resulting 7β-amino compound to form the desired 7β-acylamido group, e.g. in an analogous manner to process (A) above, followed by reduction of the 1β-oxide group later in the sequence. This is described in British Pat. No. 1,326,531. The corresponding ceph-2-em compounds may be prepared by the method of Dutch published patent application No. 6,902,013 for example by reaction of a 3-methylceph-2-em compound with N-bromosuccinimide to yield the corresponding 3-bromomethylceph-2-em compound.

Where X in formula (IV) is an acetoxy group, such starting materials may be prepared for example by acylation of 7-aminocephalosporanic acid, e.g. in an analogous manner to process (A) above. Compounds of formula (IV) in which X represents other acyloxy groups can be prepared by acylation of the corresponding 3-hydroxymethyl compounds which may be prepared for example by hydrolysis of the appropriate 3-acetoxymethyl compounds e.g. as described inter alia in British patent specifications Nos. 1,474,519 and 1,531,212.

Compounds of formula (II) may likewise be prepared in conventional manner, e.g. by nucleophilic displacement of a corresponding 3-acyloxymethyl or 3-halomethyl compound with pyridazine.

A further method for the preparation of starting materials of formula (II) comprises deprotecting the corresponding protected 7$\beta$-amino compound in conventional manner, e.g. using $PCl_5$.

It is to be noted that compounds of formula (II) are novel and constitute a further aspect of the present invention.

It should be appreciated that in some of the above transformations it may be necessary to protect any sensitive groups in the molecule of the compound in question to avoid undesirable side-reactions. For example, during any of the reaction sequences referred to above it may be necessary to protect the $NH_2$ group of the aminothiazolyl moiety, for example by tritylation, acylation (e.g. chloroacetylation), protonation or other conventional method. The protecting group may thereafter be removed in any convenient way which does not cause breakdown of the desired compound, e.g. in the case of a trityl group by using an optionally halogenated carboxylic acid such as acetic acid, formic acid, chloroacetic acid or trifluoroacetic acid or using a mineral acid, e.g. hydrochloric acid or mixtures of such acids, conveniently in the presence of a protic solvent such as water or, in the case of a chloroacetyl group, by treatment with thiourea.

Carboxyl blocking groups used in the preparation of the compounds of formula (I) or in the preparation of necessary starting materials are desirably groups which may readily be split off at a suitable stage in the reaction sequence, conveniently at the last stage. It may, however, be convenient in some instances to employ biologically acceptable, metabolically labile carboxyl blocking groups such as acyloxy-methyl or -ethyl groups (e.g. acetoxy-methyl or -ethyl and pivaloyloxymethyl groups) and retain these in the final product to give a biologically acceptable ester derivative of the compound of formula (I).

Suitable carboxyl blocking groups are well known in the art, a list of representative blocked carboxyl groups being included in British Pat. No. 1,399,086. Preferred blocked carboxyl groups include aryl lower alkoxycarbonyl groups such as p-methoxybenzyloxycarbonyl, p-nitrobenzyloxycarbonyl and diphenylmethoxycarbonyl; t-butoxycarbonyl; and lower haloalkoxycarbonyl groups such as 2,2,2-trichloroethoxycarbonyl. Carboxyl blocking group(s) may subsequently be removed by any of the appropriate methods disclosed in the literature; thus, for example, acid or base catalysed hydrolysis is applicable in many cases, as are enzymically-catalysed hydrolyses.

The following Examples illustrate the invention. All temperatures are in °C. "Ether" refers to diethyl ether. Proton magnetic resonance spectra were determined on the products at 100 MHz. The integrals were in agreement with the assignments; the signs of the coupling constants, J, in Hz, were not determined. The following abbreviations are used: s=singlet, d=doublet, m=multiplet and ABq=AB-quartet.

PREPARATION 1

Diphenylmethyl (1S, 6R, 7R)-7-Formamido-3-(pyridazinium-1-ylmethyl)ceph-3-em-4-carboxylate, 1-oxide, Bromide Salt A solution of diphenylmethyl (1S, 6R, 7R)-3-bromomethyl-7-formamidoceph-3-em-4-carboxylate, 1-oxide (4.2 g) in N,N-dimethylformamide (12 ml) was treated with pyridazine (1.34 g) and stirred for 16 hours at 22°.

The solution was treated with ether (50 ml) and tetrahydrofuran (50 ml) to give a gum which was stirred with fresh tetrahydrofuran. The resulting solid was washed with tetrahydrofuran and ether to give the title compound (4.4 g), $\nu_{max}$(Nujol) 3700 to 2700 (NH), 1796 ($\beta$-lactam), 1729 ($CO_2R$) and 1686 $cm^{-1}$ (CONH) and $\tau$(DMSO-$d_6$) 0.08 (d, J 5Hz, pyridazinium 6-H), 0.43 (d, J 5Hz, pyridazinium 3-H), 1.1 to 1.4 (m, pyridazinium 4-H and 5-H), and 3.96 and 4.18 (ABq, J 15Hz, 3-$CH_2$).

PREPARATION 2

Diphenylmethyl (1S, 6R, 7R)-7-Amino-3-(pyridazinium-1-ylmethyl)ceph-3-em-4-carboxylate, 1-oxide, Hydrochloride/Bromide Salt The product from Preparation 1 (0.583 g) was stirred with methanol (5 ml) at 0° to give a gummy solid.

The mixture was treated with phosphoryl chloride (0.46 g). A solution was obtained after 15 minutes and stirring was continued below 10° for 2 hours.

Dropwise addition of the above solution to ether (60 ml) gave a gummy solid which was stirred with ethyl acetate (40 ml) for 30 minutes. The product was collected and washed with ether to give the title compound (0.43 g) as a solid, $\lambda_{max}$(EtOH) 274 nm ($E_{1\ cm}^{1\%}$ 123) and $\nu_{max}$(Nujol) 3420 ($H_2O$), 3700 to 2100 ($NH_3\oplus$), 1802 ($\beta$-lactam), 1729 ($CO_2R$) and 1028 $cm^{-1}$ (S→0).

EXAMPLE 1

(a) Diphenylmethyl (1S, 6R, 7R)-7-[(Z)-2-(2-t-Butoxycarbonylprop-2-oxyimino)-2-(2-tritylaminothiazol-4-yl)acetamido]-3-(pyridazinium-1-ylmethyl)ceph-3-em-4-carboxylate, 1-oxide, Bromide Salt A solution of diphenylmethyl (1S, 6R, 7R)-3-bromomethyl-7-[(Z)-2-(2-t-butoxycarbonylprop-2-oxyimino)-2-(2-tritylaminothiazol-4-yl)-acetamido]-ceph-3-em-4-carboxylate, 1-oxide (1.24 g) in dry tetrahydrofuran (6 ml) was treated with pyridazine (0.088 ml) and the solution was stirred at 24° for 2 hours then left to stand at ca 20° for 30 hours.

The reaction mixture was added slowly to stirred ether (150 ml) and the lilac precipitate was filtered off and washed with ether and dried in vacuo to give the title ester (1.10 g) as a solid, m.p. 147° to 154° (with decomposition), $\lambda_{inf}$ (EtOH) 240 nm ($E_{1\ cm}^{1\%}$ 231, $\epsilon$ 26,400), 265 nm ($E_{1\ cm}^{1\%}$ 90, $\epsilon$ 10,400) and 305 nm ($E_{1\ cm}^{1\%}$ 67, $\epsilon$ 7,650).

(b) Diphenylmethyl (6R, 7R)-7-[(Z)-2-(2-t-Butoxycarbonylprop-2-oxyimino)-2-(2-tritylaminothiazol-4-yl)acetamido]-3-(pyridazinium-1-ylmethyl)ceph-3-em-4-carboxylate, Iodide and Bromide Salts A cooled (−10°) and stirred mixture of the product from (a) (1.00 g) and potassium iodide (0.600 g) in acetone (5 ml) was treated with acetyl chloride (0.13 ml) and the mixture was stirred at 0° to +2° for 1 hour.

The product was added slowly to a stirred solution of sodium metabisulphite (0.8 g) in water (80 ml) and the resultant precipitate was filtered off, washed with water and dried in vacuo over phosphorus pentoxide to give a solid (0.989 g).

A similar reduction sequence using potassium iodide (0.600 g), acetone (5 ml) and acetyl chloride was repeated on the above product and the resultant precipitate was filtered off, washed with water and dried in vacuo over phosphorus pentoxide to give a solid (1.0 g).

The solid was partitioned between ethyl acetate (containing dichloromethane) and aqueous sodium metabisulphite solution and the organic phase was separated and washed with water and dried and evaporated to give a foam which, on trituration with ether, gave the title compound (0.87 g) as a solid; $[\alpha]_D -20°$ (c 0.25, CHCl$_3$), $\lambda_{infl.}$ (EtOH) 238 nm (E$_{1\ cm}^{1\%}$ 265, $\epsilon$ 29,400), 264 nm (E$_{1cm}^{1\%}$ 160, $\epsilon$ 17,700) and 299 nm (E$_{1cm}^{1\%}$ 81, $\epsilon$ 9,000).

(c) (6R, 7R)-7-[(Z)-2-(2-Aminothiazol-4-yl)-2-(2-carboxyprop-2-oxyimino)acetamido]-3-(pyridazinium-1-ylmethyl)ceph-3-em-4-carboxylate The product of stage (b) (0.77 g) was dissolved in anisole (0.8 ml) and trifluoroacetic acid (3.2 ml) was added. The mixture was swirled at 22° for 3 minutes and then evaporated in vacuo to give a liquid. Trituration of this liquid with ether gave a precipitate which was filtered off and washed with ether and dried in vacuo to give a solid (0.54 g).

This solid was wetted with anisole (0.12 ml) and then treated with trifluoroacetic acid (15 ml). The solution (containing a slight suspension) was swirled at 22° for 15 minutes. The mixture was filtered and the filtrate was evaporated to an oil, which, on trituration with ether: ethyl acetate (2:1) afforded a precipitate.

The precipitate was filtered off and washed with ether and dried in vacuo to give the title compound associated with 1.5 moles of trifluoroacetic acid (0.468 g), $\lambda_{max}$ (pH 6 buffer) 237 nm (E$_{1\ cm}^{1\%}$ 295, $\epsilon$ 19,800) and $\lambda_{infl}$ 295 nm (E$_{1\ cm}^{1\%}$ 117, $\epsilon$ 8,600), $\nu_{max}$ (Nujol) 3700 to 2200 (NH, NH$_2$ and OH), 1786 ($\beta$-lactam), 1720 (sh) (free acid) and 1670 cm$^{-1}$ (CO$_2^-$).

EXAMPLE 2

(6R, 7R)-7-[(Z)-2-(2-Aminothiazol-4-yl)-2-(2-carboxyprop-2-oxyimino)acetamido]-3-(pyridazinium-1-ylmethyl)-ceph-3-em-4-carboxylate, sodium salt (6R, 7R)-3-Acetoxymethyl-7-[(Z)-2-(2-aminothiazol-4-yl)-2-(2-carboxyprop-2-oxyimino)acetamido]ceph-3-em-4-carboxylic acid (0.264 g), sodium hydrogen carbonate (0.105 g), sodium iodide (0.9 g), pyridazine (0.073 ml) and water (0.2 ml) were heated together at 76° for 2¼ hours.

The solution was allowed to cool and the resulting solid was dissolved by warming with water (0.6 ml). The solution was added dropwise to stirred acetone (150 ml) and the precipitate was filtered off and washed with acetone and ether and was dried in vacuo to give the title compound (0.284 g) as a solid. $\tau$(D$_2$O) 0.24 (m, pyridazinium 6-H), 0.60 (m, pyridazinium 3-H), 1.4–1.7 (broad m, pyridazinium 4- and 5-H) 3.11 (s, thiazole 5-H), 4.1–4.6 (obscured ABq, 3-CH$_2$), 4.21 (d, J 5Hz, 7-H), 4.79 (d, J 5Hz, 6-H), 6.27 and 6.55 (ABq J 18Hz, 2 - H$_2$) 8.55 (s, CMe$_2$).

EXAMPLE 3

(6R, 7R)-7-[(Z)-2-(2-Aminothiazol-4-yl)-2-(1-carboxycyclobut-1;-oxyimino)acetamido]-3-(pyridazinium-1-ylmethyl)-ceph-3-em-4-carboxylate, sodium salt (6R, 7R)-3-Acetoxymethyl-7-[(Z)-2-(2-aminothiazol-4-yl)-2-(1-carboxycyclobut-1-oxyimino)acetamido]-ceph-3-em-4-carboxylic acid (0.54 g), sodium hydrogen carbonate (0.21 g), sodium iodide (1.8 g), pyridazine (0.21 ml) and water (0.35 ml) were heated together at 80° for 1.25 hours. The solution was allowed to cool and the resulting solid was dissolved by warming with water (ca. 0.5 ml). The solution obtained was added slowly to stirred acetone (100 ml) and the precipitate was filtered off, washed with acetone and dried in vacuo to give a solid (0.618 g).

This solid was purified on a column of XAD-2 resin (100 g) eluted in 66 ml fractions. Elution was with water (fractions 1 to 11) then water:ethanol (3:1) (fractions 12 to 18). Fractions 12 to 17 were combined and evaporated to ca. 250 ml and freeze-dried to a foam which, on trituration with ether gave the title compound (0.229 g) as a solid, $[\alpha]_D +19°$ (c 0.64, H$_2$O), $\lambda_{max}$(pH6 buffer) 242 nm (E$_{1\ cm}^{1\%}$ 302) with an inflection at 290 nm (E$_{1\ cm}^{1\%}$ 154).

EXAMPLE 4

Diphenylmethyl (1S, 6R, 7R)-7-[(Z)-2-(2-t-Butoxycarbonyl-prop-2-oxyimino)-2-(2-tritylaminothiazol-4-yl)-acetamido]-3-(pyridazinium-1-ylmethyl)ceph-3-em-4-carboxylate, 1-oxide, Bromide Salt Phosphorus pentachloride (0.11 g) in dry dichloromethane (10 ml) at 0° was treated with (Z)-2-(2-t-butoxycarbonylprop-2-oxyimino)-2-(2-tritylaminothiazol-4-yl)acetic acid (0.295 g) and the solution was stirred for 35 minutes at 0°. Triethylamine (0.16 ml) was added and stirring was continued for 5 minutes at 0°.

The resulting solution was added, dropwise, over 5 minutes to a vigorously stirred suspension of the product of Prep. 2 (0.301 g) in dichloromethane (15 ml) at 0°. The suspension was stirred with cooling for 15 minutes and without cooling for 1 hour. The mixture was left at 0° for 15 hours then poured into ethyl acetate (100 ml) and water (100 ml). The organic phase was washed with water then dried and evaporated in vacuo to a foam which, on stirring with ether gave the title compound (0.13 g) as an amorphous solid. The ether liquors were evaporated to give further product (0.23 g).

The first crop of material had $\lambda_{inf}$(EtOH) at 240 nm (E$_{1\ cm}^{1\%}$ 253), 265 nm (E$_{1\ cm}^{1\%}$ 181) and 305 nm (E$_{1\ cm}^{1\%}$ 76) and $\nu_{max}$(CHBr$_3$) 3500 to 3000 (NH), 1802 ($\beta$-lactam); 1725 (esters), and 1680 and 1520 cm$^{-1}$ (CONH).

The title compound may be converted into (6R, 7R)-7-[(Z)-2-(2-aminothiazol-4-yl)-2-(2-carboxyprop-2-oxyimino)acetamido]-3-(pyridazinium-1-ylmethyl)-ceph-3-em-4-carboxylate, by the methods described in Examples 1(b) and 1(c).

PHARMACEUTICAL FORMULATIONS

The antibiotic compounds of the invention may be formulated for administration in any convenient way, by analogy with other antibiotics and the invention therefore includes within its scope pharmaceutical compositions comprising an antibiotic compound in accordance with the invention adapted for use in human or veterinary medicine. Such compositions may be presented for use in conventional manner with the aid of any necessary pharmaceutical carriers or excipients.

The antibiotic compounds according to the invention may be formulated for injection and may be presented in unit dose form in ampoules, or in multi-dose containers if necessary with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form for constitution with a suitable vehicle, e.g. sterile, pyrogen-free water, before use.

If desired, such powder formulations may contain an appropriate non-toxic base in order to improve the water-solubility of the active ingredient and/or to ensure that when the powder is constituted with water, the pH of the resulting aqueous formulation is physiologically acceptable. Alternatively the base may be present in the water with which the powder is constituted. The base may be for example an inorganic base such as sodium carbonate, sodium bicarbonate or sodium acetate or an organic base such as lysine or lysine acetate.

The antibiotic compounds may also be formulated as suppositories e.g. containing conventional suppository bases such as cocoa butter or other glycerides.

For medication of the eyes or ears, the preparations may be formulated as individual capsules, in liquid or semi-solid form, or as drops.

Compositions for veterinary medicine may also, for example, be formulated as intramammary preparations in either long acting or quick-release bases.

The compositions may contain from 0.1% upwards, e.g. 0.1 99% of the active material, depending on the method of administration. When the compositions comprise dosage units, each unit will preferably contain 50–1500 mg of the active ingredient. The dosage as employed for adult human treatment preferably ranges from 250 to 6000 mg per day, depending on the route and frequency of administration. For example, in adult human treatment 1000 to 3000 mg per day administered intravenously or intramuscularly should normally suffice. In treating Pseudomonas infections higher daily doses may be required.

The antibiotic compounds according to the invention may be administered in combination with other therapeutic agents such as antibiotics, for example penicillins or other cephalosporins.

The following formulations illustrate how the compounds according to the invention may be made up into pharmaceutical formulations.

Formulation—For Injection

Fill sterile (6R,7R)-7-[(Z)-2-(2-aminothiazol-4-yl)-2-(2-carboxyprop-2-oxyimino) acetamido]-3-(pyridazinium-1-ylmethyl)ceph-3-em-4-carboxylate monosodium salt into glass vials, such that each vial contains an amount equivalent to 500 mg of the antibiotic acid. Carry out the filling aseptically under a blanket of sterile nitrogen. Close the vials using rubber discs, or plugs, held in position by aluminium overseals, thereby preventing gaseous exchange or ingress of microorganisms. Constitute the product by dissolving in Water for Injections or other suitable sterile vehicle shortly before administration.

(6R,7R)-7-[(Z)-2-(2-Aminothiazol-4-yl)-2-(1-carboxycyclobut-1-oxyimino) acetamido]-3-(pyridazinium-1-yl-methyl) ceph-3-em-4-carboxylate may also be formulated for injection in the manner described above.

We claim:

1. A cephalosporin antibiotic selected from the group consisting of compounds of formula:

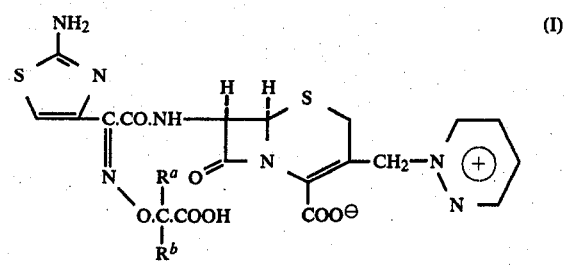

wherein $R^a$ and $R^b$, which may be the same or different, each represents a $C_{1-4}$ alkyl group, or together with the carbon atom to which they are attached form a $C_{3-7}$ cycloalkylidene group and non-toxic salts thereof.

2. A compound as claimed in claim 1 wherein $R^a$ and $R^b$ each represents a methyl or ethyl group.

3. A compound as claimed in claim 1 wherein $R^a$ and $R^b$ together with the carbon atom to which they are attached form a $C_{3-5}$ cycloalkylidene group.

4. A compound as claimed in claim 1 which is (6R,7R)-7-[(Z)-2-(2-aminothiazol-4-yl)-2-(2-carboxyprop-2-oxyimino)acetamido]-3-(pyridazinium-1-ylmethyl)ceph-3-em-4-carboxylate.

5. A non-toxic salt of the compound of claim 4.

6. A compound as claimed in claim 1 which is (6R,7R)-7-[(Z)-2-(2-aminothiazol-4-yl)-2-(1-carboxycyclobut-1-oxyimino)acetamido]-3-(pyridazinium-1-ylmethyl)ceph-3-em-4-carboxylate.

7. A non-toxic salt of the compound of claim 6.

8. A pharmaceutical composition for use in human or veterinary medicine comprising an effective amount of at least one antibiotic compound of claim 1 in association with a pharmaceutical carrier or excipient.

9. A method of combatting a bacterial infection in a human or a warm-blooded animal comprising administering an antibacterially effective amount of at least one compound of claim 1.

* * * * *